United States Patent [19]

Braginsky et al.

[11] Patent Number: 5,585,569

[45] Date of Patent: Dec. 17, 1996

[54] APPARATUS AND METHOD FOR EVALUATING THE STABILITY OF A DISPERSE SOLID MATERIAL AGAINST CAKING

[75] Inventors: Leonid Braginsky; Yuri Kokotov, both of Maaleh Edomim; Reuven Wachs, Jerusalem, all of Israel

[73] Assignee: Temech Chemical Engineering Ltd., Jerusalem, Israel

[21] Appl. No.: 499,212

[22] Filed: Jul. 7, 1995

[30] Foreign Application Priority Data

Jul. 10, 1994 [IL] Israel ........................................ 110266

[51] Int. Cl.$^6$ ........................................ G01N 3/08
[52] U.S. Cl. ................................ 73/821; 73/818
[58] Field of Search ............................ 73/788, 790, 818, 73/819, 821, 825

[56] References Cited

U.S. PATENT DOCUMENTS

| | | | |
|---|---|---|---|
| 3,890,830 | 6/1975 | Dyck | 73/825 |
| 4,161,114 | 7/1979 | Kraeutle | 374/46 |
| 4,179,916 | 12/1979 | Konnerth | 73/866 |
| 4,716,768 | 1/1988 | David et al. | 73/861 |
| 5,397,994 | 3/1995 | Phare | 324/668 |

OTHER PUBLICATIONS

The Storage and Flow of Powders by J. C. Williams; Principles of Powder Technology pp. 91–119.

A Method of Evaluating the Mechanical Characteristics of Powders from the Determination of the strength of Compacts by Newton et al.; Powder Technology, 72 (1992) pp. 97–99. Jan. 1992.

*Primary Examiner*—Richard Chilcot
*Assistant Examiner*—Max H. Noori
*Attorney, Agent, or Firm*—Brumbaugh, Graves, Donohue & Raymond

[57] ABSTRACT

An apparatus and a method for evaluating the stability of a disperse solid material against caking. The apparatus includes a chamber for storing a sample of the disperse solid material, the chamber having a diverging cross sectional area along a line of action of a compression load compressing the sample so as to cake a portion of the sample and an opening for enabling separation of the uncaked portion of the sample from the caked portion of the sample, a shutter for selectively sealing the opening during partial aggregation of the sample and a compression load mechanism for applying the compression load. The method includes the steps of providing a known weight of a sample of a disperse solid material, applying a compression load so as to cake a portion of the sample, separating an uncaked portion of the sample from a caked portion of the sample after partial aggregation of the sample and computing an index for the stability of the disperse solid material against caking.

3 Claims, 2 Drawing Sheets

# APPARATUS AND METHOD FOR EVALUATING THE STABILITY OF A DISPERSE SOLID MATERIAL AGAINST CAKING

FIELD OF THE INVENTION

The invention relates to an apparatus and a method for evaluating the stability of a powdered material or granulated material against caking. For the sake of convenience, both powdered materials and granulated materials will be referred to herein collectively as "disperse solid materials".

BACKGROUND OF THE PRESENT INVENTION

It is well known that disperse solid materials have the undesirable tendency of caking or aggregating during storage and/or transportation. Furthermore, it is well known that the tendency of caking is dependent on a number of factors, for example, ambient conditions, the shape of a container, and the like.

Conventional methods of evaluating the stability of disperse solid materials against caking can be divided into two approaches. In one approach, a disperse solid material is evaluated by measuring the smallest compression load required to aggregate a sample of material. In another approach, a disperse solid material is evaluated by measuring a particular mechanical characteristic of an aggregate formed as a result of the compression of a sample of material by a known compression load.

One method applying the first approach is known as the Newton method and involves applying a compression load to a sample of a disperse solid material and concurrently measuring a decrease in the volume of the sample. The stability of the material against caking is deduced from the compression load at which no further decrease in volume occurs. The method is described in an article entitled "A Method of evaluating the mechanical characteristics of powder from the determination of the strength of compacts" by Newton G. M. et al., Powder Technology, 1992, Vol. 72, No. 1, pp. 97–99.

Generally speaking, the methods applying the first approach suffer from the disadvantage that the transition from a disperse state to an aggregate state is a gradual process and therefore there exists considerable discrepancy as i to the "degree of caking", and the corresponding compression load which achieved that degree of caking, which is sufficient for a sample to be regarded as having been aggregated.

One method applying the second approach is known as the Jenike method and involves determining the relation between the compression load employed to aggregate a sample and the shear stress required to shear the aggregate. The Jenike method is described in a book entitled "Principles of Powder Technology", John Wiley & Sons, N.Y., 1990, pp. 91–118.

Another method applying the second approach is described by Andrianov, Certificate of Authorship of the USSR, No. 752153, Inventions and Discoveries, 1980, No. 28 and involves placing a sample of a solid disperse material in a cylindrical :chamber, applying a pre-determined pressure, typically 50 kPa, to the sample, maintaining the sample at a temperature of 350° C. and measuring the tear stress of the resulting aggregate.

Generally speaking, the methods applying the second approach suffer from the disadvantage that a mechanical characteristic of an aggregate is not a metric of the stability against caking of a disperse solid material but rather a metric of the aggregate itself.

It is also well known that solutions to overcome the tendency of caking include selection of the particle size of the disperse material, adding anti-caking agents, and the like.

The method most widely used for selection and comparison of anti-caking agents includes applying compression loads to samples of material mixed with the same proportion by mass of different anti-caking agents. The efficiency of each anti-caking agent can be deduced from the compression load required to cause caking, namely, the efficiency of the anti-caking agent is higher if a greater compression load is required to aggregate a sample. This method applies the first approach described hereinabove and therefore suffers from the same disadvantage.

BRIEF SUMMARY OF THE INVENTION

The present invention is for an apparatus and a method for evaluating the stability of disperse solid materials against caking. The present application has a wide range of applications including quality control of a manufacturer or an end user, the evaluation of anti-caking agents, the evaluation of optimum ambient conditions for transportation and storage purposes, and the like.

While not wishing to be bound by theory, it is believed that caking of a disperse solid material occurs at a threshold caking pressure under given ambient conditions. Furthermore, it is believed that the threshold caking pressure of a material is dependent on a number of factors including, for example, the particle size of the material, the ambient humidity, the ambient temperature, and other factors.

The present invention takes advantage of the threshold caking pressure of a material so as to arrive at indices indicating the relative stability of a disperse solid material against caking. In practice, this is achieved by applying a compression load to a sample having a diverging cross sectional area in the line of action of a compressive load so as to cake the part of the sample under a local pressure which is greater than or substantially equal to the threshold caking pressure of the material. In other words, for a given compression load, a sample having a diverging cross sectional area will cake until .the cross sectional area of the sample is such that the pressure acting on the material is substantially equal to or less than the threshold caking pressure.

One of the ways to achieve a sample having a diverging cross sectional area is by the provision of a chamber having a diverging cross sectional area. Another way to provide a sample having a cross sectional area is by providing by chamber having a cylindrical cross sectional area and a member having a converging cross sectional area for applying the compression load.

Thereafter, an index indicating the relative stability against caking can be arrived at by calculating the weight of the uncaked portion of the sample to the total weight of the sample. It should be noted that as the index, in this case the ratio, approaches unity, so the material has an increased resistance against caking. Alternatively, an index indicating the relative stability against caking can be arrived at by calculating the weight of the uncaked portion of a sample to the weight of the caked portion of the sample. More complex indices can take into account factors such as parameters of the material, the compression load, the time of compression, the ambient conditions, and the like for comparison of different materials. It can be readily appreciated that these indices can also provide information regarding the efficiency of anti-caking agents.

Thus, there is provided in accordance with the teachings of the present invention, an apparatus for evaluating the stability of a disperse solid material against caking, the apparatus comprising: (a) a chamber for storing a sample of the disperse solid material, the chamber having a diverging cross sectional area along a line of action of a compression load compressing the sample so as to cake a portion of the sample and a sealable opening for enabling separation of an uncaked portion of the sample from a caked portion of the sample after a partial aggregation of the sample; (b) a shutter for selectively sealing the opening during the partial aggregation of the sample; and (c) a compression load mechanism for applying the compression load.

Preferably, the opening is the large cross sectional diameter end of the cone, the member is cone-shaped and the chamber has an inner surface provided with a series of transversely directed ribs directed towards the interior of the chamber for trapping the caked portion of the sample in the chamber.

The apparatus can also include a device for regulating the temperature of the sample and means for regulating the humidity of the sample.

There is also provided in accordance with the teachings of the present invention, a method for evaluating the stability of a disperse solid material against caking, the method comprising the steps of: (a) providing a known weight of a sample of a disperse solid material; (b) applying a compression load so as to cake a portion of the sample; (c) separating an uncaked portion of the sample from a caked portion of the sample after the partial aggregation of the sample; and (d) computing an index for the stability of the disperse solid material against caking.

BRIEF DESCRIPTION OF THE DRAWINGS

For a better understanding of the present invention and to show how the same can be carried out in practice, reference will now be made, by way of example, to the accompanying drawings in which.

DETAILED DESCRIPTION OF PREFERRED EMBODIMENTS OF THE PRESENT INVENTION

Figure 1:
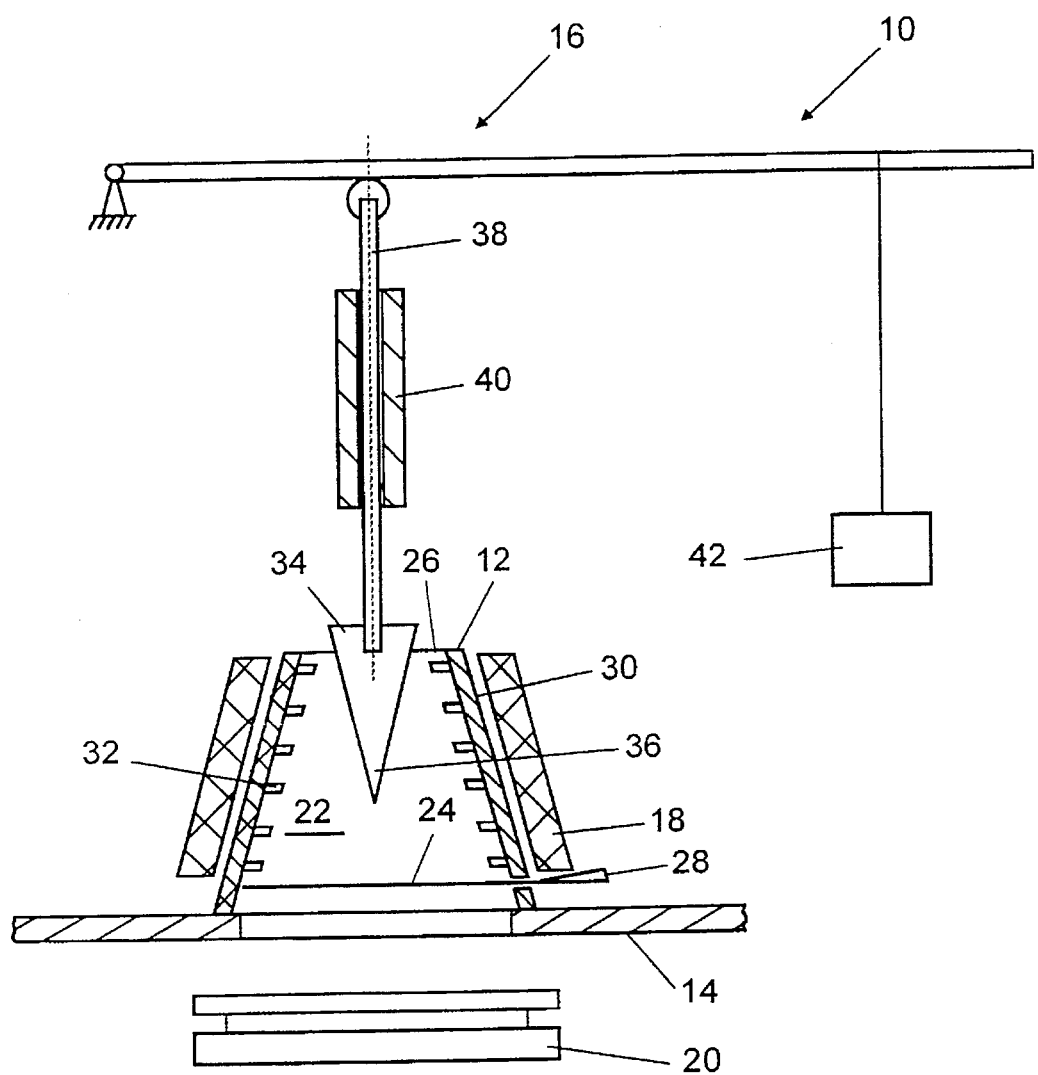
FIG. 1 is a cross sectional view of an apparatus for evaluating the stability of disperse solid materials against caking in accordance with a preferred embodiment of the present invention.

With reference now to the drawings, FIG. 1 depicts an apparatus, general designated 10, for evaluating the stability of a disperse solid material against caking in accordance with a preferred embodiment of the present invention.

The apparatus 10 includes a chamber 12 for storing a sample of disperse solid material under test, a generally annular stand 14 for supporting the chamber 12, a compression load mechanism 16 for applying a compression load to the sample, a device 18 for regulating the temperature of the sample, a balance 20 for weighing an uncaked portion of a sample and a means (not shown) for regulating the humidity of the sample.

The chamber 12 is preferably fashioned as a hollow truncated cone 22 having a lower large cross sectional area end 24 and an upper large cross sectional area end 26. The end 24 is preferably employed as an opening through which the uncaked portion of a sample passes for collection on the balance 20 after the partial aggregation of the sample and, as such, is therefore selectively sealed by a shutter 28. The end 26 can be sealed by a removable lid (not shown) so as to enable the filling of the chamber 12 when inverted, thereby ensuring a better packing of the sample in the chamber 12 by enabling the chamber 12 to be filled from its end 24. Alternatively, in the case that the chamber 12 is disposable, then the lid can be made from a relatively thin material which can be readily punctured as will become apparent hereinbelow.

The chamber 12 has an inner surface 30 which is best provided with a series of transversely directed ribs 32 extending into the interior of the chamber 12 for trapping the caked portion of a sample in the chamber 12 after the shutter 28 has been opened. The length of a rib 32 is preferably equal to at least 0.02 of its radius of curvature.

The chamber 12 can be designed for repeated use or, alternately, as a throw away disposable item. It can therefore be fabricated from a wide range of materials including, but not limited to, metal, plastic, stiffened paper, and the like.

The compression load mechanism 16 includes a displaceable member 34, preferably fashioned as a cone shaped piston 36 for puncturing a lid in the case that the chamber 12 is disposable. The member 34 is driven by a rod 38 traversing a guide bush 40 and weighted by a load 42. Alternatively, the compression load mechanism 16 can be implemented by any one of a wide range of other conventional compression load mechanisms including, but not limited to, pneumatic mechanisms, hydraulic mechanisms, electro-magnetic mechanisms, and the like.

It can be readily appreciated that the apparatus 10 can be modified in other ways to cater for a wide range of different disperse solid materials. Such modifications can include, but are not limited to, varying the divergence angle of the chamber 12, varying the convergence angle of the displaceable member 34, and the like.

It should be noted that in an alternate embodiment of apparatus 10, the chamber 12 can be fashioned with a generally cylindrical cross sectional area in which the diverging cross sectional area of the sample is achieved by means of the displaceable member 34 having a generally converging cross sectional area so as to define a generally diverging cross sectional area channel between the chamber 12.

The operation of the apparatus 10 is now described.

The chamber 12 is filled with a sample of known weight of a disperse solid material under investigation, the shutter 28 is closed so as to seal the chamber 12 and the chamber 12 is inverted and placed on the annular stand 14. The sample is heated or cooled to a prescribed temperature, if necessary.

Then, a pre-determined compression load is applied to the sample for a pre-determined period of time by means of the load compression mechanism 16 so as to aggregate a portion of the sample in the part of the chamber 12 in which the local pressure is greater than the threshold caking pressure of the material under the prevailing ambient conditions. It should be noted that the caked portion of the sample typically extends from the top part of the chamber 12 towards the bottom part of the chamber 12.

Thereafter, the load is removed from the sample and the shutter 28 is opened, thereby enabling the uncaked portion of the sample to pour onto the balance 20 and leaving the caked portion of the sample in the upper part of the chamber 12, typically trapped by one of the ribs 32.

Finally, an index for evaluating the relative stability of the sample is calculated. As mentioned above, the index can be the weight of the uncaked portion of the sample to the total weight of the sample, the weight of the uncaked portion of the sample to the weight of the caked portion of the sample, or a more complicated index taking into consideration other factors.

It can be readily appreciated that the apparatus and the method of the present invention can be applied to a wide range of applications including, but not limited to, prediction of behavior of materials in hoppers, the investigation of the influence of temperature and humidity on the caking tendency of stored materials, the evaluation of quality of products by manufacturers or consumers, and the like. For the sake of exposition only, three applications of the apparatus and the method of the present invention are presented hereinbelow.

Example 1 Evaluation of the stability of the detergent powder B against caking during transportation and storage in standard boxes.

The stability of the detergent powder B against caking was evaluated by comparison to a detergent powder A which has a different formulation from that of detergent powder B and is known not to aggregate during transportation and storage in standard boxes in the following manner:

Table 1 presents the results for three tests in which a known weight of detergent powder A was subjected to a given load for 5 min. The mean value of the ratio F of the weight of the uncaked portion of the sample to the total weight of the sample is 0.62.

Table 2 presents the results for three tests in which a known weight of detergent powder B was subjected to the same load for the same length of time. The mean value of the ratio F of the weight of the uncaked portion of the sample to the total weight of the sample is 0.67.

TABLE 1

Results of detergent powder A

The sample

| No. of the sample | Total weight G, g | Weight of uncaked portion Q, g | Parameter F = Q/G |
|---|---|---|---|
| 1 | 42.3 | 26.4 | 0.624 |
| 2 | 43.1 | 27.0 | 0.626 |
| 3 | 42.2 | 25.7 | 0.609 |

The mean value of F = (0.624 + 0.626 + 0.609)/3 = 0.62

TABLE 2

Results of detergent powder B

The sample

| No. of the sample | Total weight G, g | Weight of uncaked portion Q, g | Parameter F = Q/G |
|---|---|---|---|
| 1 | 43.3 | 28.9 | 0.667 |
| 2 | 42.4 | 29.8 | 0.703 |
| 3 | 42.8 | 27.7 | 0.647 |

The mean value: F = (0.667 + 0.703 + 0.647)/3 = 0.672

The parameter F for the tested detergent powder B is higher than that for the detergent powder A under the same ambient conditions teaching that the stability of the detergent powder B against caking is greater than that of detergent powder A. Thus, the detergent powder B will also preserve its disperse state during transportation and storage in standard boxes.

Example 2 Evaluation of the efficiency of an anti-caking agent

The price of an anti-caking agent is relatively high and it was therefore deemed necessary to determine the most cost effective amount of anti-caking agent E needed by mass without diminishing the stability of a powder product D against caking.

Figure 2:
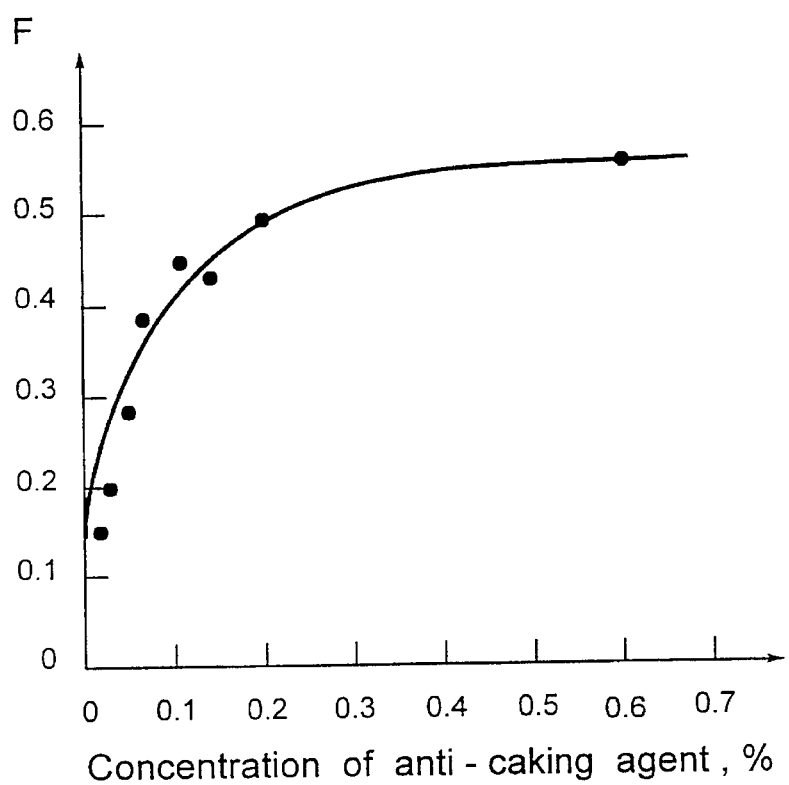
FIG. 2 is a graph for evaluating the efficiency of an anti-caking agent.

FIG. 2 presents the results of a series of measurements carried out on a number of samples of powdered chemical D mixed with different proportions of anti-caking agent within the range of 0% to 0.8% by mass.

The graph clearly teaches that the stability of the powder material D is highly sensitive to the concentration of the anti-caking agent E at low concentrations of up to about 0.25% by mass and is less sensitive to the concentration of the anti-caking agent E at high concentrations of greater than about 0.25% by mass. Thus, in this case, the most cost effective concentration of the anti-caking agent E for powder material D is within the region of about 0.20% to 0.25% by mass.

Figure 3:
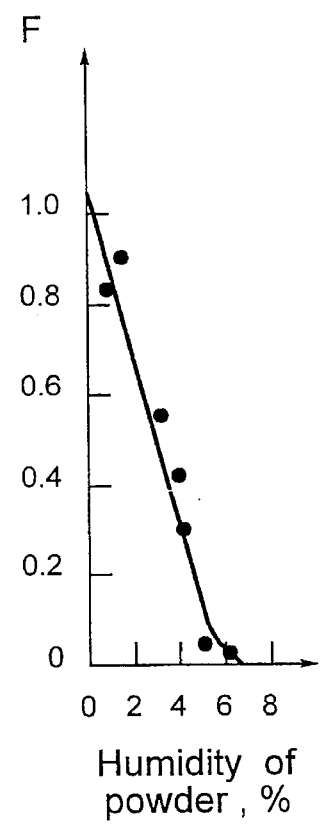
FIG. 3 is a graph for evaluating the effect of humidity on the stability of a disperse solid material against caking.

Example 3: Evaluation of the effect of humidity on the stability of a product against caking A product M is known to be hygroscopic and it was therefore deemed necessary to determine how an increase in humidity would affect the tendency for caking during long term storage. FIG. 3 presents the results of a series of measurements carried out on samples of the product M at different levels of humidity within the range of 0% to 6% by mass. The graph clearly teaches that even a small increase in humidity results in a significant loss of the product's stability against caking.

While the invention has been described with respect to a limited number of embodiments, it will be appreciated that many variations, modifications and other applications of the invention can be made by those ordinarily skilled in the art.

We claim:

1. A method for evaluating the stability of a disperse solid material against caking, the method comprising the steps of:
   (a) providing a known weight of a sample of a disperse solid material;
   (b) applying a compression load so as to cake a portion of the sample;
   (c) separating an uncaked portion of the sample from a caked portion of the sample after partial aggregation of the sample; and (d) computing an index for the stability of the disperse solid material against caking.

2. The method according to claim 1, further comprising the step of regulating the temperature of the sample.

3. The method according to claim 1, further comprising the step of regulating the humidity of the sample.

* * * * *